United States Patent [19]
Duffner

[11] Patent Number: 6,043,074
[45] Date of Patent: Mar. 28, 2000

[54] *DESULFUROCOCCUS AMYLOPULLULANASE*

[75] Inventor: Fiona Duffner, København, Denmark

[73] Assignee: Novo Nordisk A/S, Bagsvaerd, Denmark

[21] Appl. No.: 09/306,922

[22] Filed: May 7, 1999

[51] Int. Cl.[7] .............................. C12N 9/24; C12N 9/26; C12N 9/42; C12N 1/20; C07H 21/04
[52] U.S. Cl. .................... 435/200; 435/201; 435/209; 435/252.3; 435/320.1; 536/23.2
[58] Field of Search ..................... 435/200, 201, 435/209, 252.3, 320.1; 536/23.2

[56] References Cited

U.S. PATENT DOCUMENTS 4,287,304  9/1981  Muller et al. ........................... 435/162

FOREIGN PATENT DOCUMENTS

WO 95/23853  9/1995  WIPO .

OTHER PUBLICATIONS

Canganella et al. (1994) Appl. Microbiol. Biotechnol., vol. 42, pp. 239–245.
Tibech, vol. 10. Sep. 1992, Don A. Cowan, "Biotechnology of the Archaea", pp. 315–323.
National Library of Medicine (NLM), Medline, Medline Accession No. 94079331, Adams MW.
Abstract –Dailog, File 357, Derwent Biotechnology Abs, Dialog Accession No. 170578.
Abstract –Dialog, File 55, Biosis Previews, Dialog Accession No. 11491261, Biosis No. 98091261.
Bragger et al., Appl. Microbiol. Biotechnol. 31: 556–561, 1989.

*Primary Examiner*—Ponnathapu Achutamurthy
*Assistant Examiner*—Elizabeth Slobodyansky
*Attorney, Agent, or Firm*—Steve T. Zelson; Valeta Gregg

[57] ABSTRACT

The present invention relates to *Desulfurococcus amylopullulanase* preparations and their use in producing sweeteners and ethanol from starch.

6 Claims, 5 Drawing Sheets

DESULFUROCOCCUS AMYLOPULLULANASE

FIELD OF INVENTION

The present invention relates to a novel thermostable enzyme having amylase and pullulanase activities, and use in the production of sweeteners and ethanol from starch. Further the invention relates to the cloned and isolated nucleic acid sequence encoding the thermostable enzyme having amylase and pullulanase (herein termed "amylopullulanase") of the invention, nucleic acid constructs, recombinant expression vectors, and recombinant host cells comprising the nucleic acid construct of the invention and methods for producing a mutant nucleic acid sequence of the invention; a mutant nucleic acid sequence produced by the method of the invention, and a method for producing a recombinant thermostable amylopullulanase of the invention.

BACKGROUND OF THE INVENTION

The production of sweeteners from starch has been largely improved by application of different microbial enzymes to obtain better quality and yields, but the necessity of performing several steps of the starch-hydrolysing process at elevated temperatures means that there is still a need for new starch-hydrolysing enzymes with increased thermal stability.

It is known that Pyrococcus, e.g., *Pyrococcus wosei* and *Pyrococcus furiosus*, for reference see *Arch. Microbiol.* 155, 1991, pp. 572–578, and *Appl. Env. Microbiol.* 56, 1990, pp.1985–1991, can produce highly thermostable amylases.

It is the object of this invention to provide an amylase and a pullulanase with temperature optimum at 80° C. or above 80° C.

SUMMARY OF THE INVENTION

We have found that novel thermostable enzymes having amylase and pullulanase activity can be obtained from *Desulfurococcus mucosus*, a strain not previously reported to produce thermostable enzymes having amylase and pullulanase activity; these new enzymes have temperature optimum around 100° C.

Accordingly, the invention provides an amylopullulanase preparation, characterised by being producible by cultivation of an amylopullulanase producing strain of *Desulfurococcus mucosus*.

Cloning of the amylopullulanase gene from *Desulfurococcus mucosus* As described below, the amylopullulanase from the hyperthermophilic archaeon

*Desulfurococcus mucosus* was cloned in *E. coli*. This high temperature enzyme is active on starch, pullulan, synthetic amylose, maltohexaose, glycogen, α-cyclodextrin and β-cyclodextrin as seen using TLC analysis. A spot running at G3 (maltotriose) is produced from pullulan.

The sequence of the amylopullulanase gene demonstrated low homology (less than 30% amino acid identity) to the maltoamylase sequence from *Bacillus acidopullulyticus* (28.7%); 27.9% amino acid identity to the cyclomaltodextrin hydrolase from *Thermoanaerobacter ethanolicus* (Podkovyrov and Zeikus, 1992); and 27% amino acid identity to the neopullulanase from *Bacillus stearothermophilus*. The four conserved regions found in amylolytic enzymes are present in the cloned amylopullulanase from *Desulfurococcus mucosus*. The DNA sequence of the amylopullulanase of the invention bears little discernible resemblance to the amylopullulanase from *P. furiosus*. Other ORF's in the insert showed weak homology to hypothetical proteins from Aquifex (hyperthermophilic bacterium) and Streptomyces.

The present invention relates to isolated nucleic acid sequences encoding polypeptides having amylopullulanase activity, selected from the group of:

(a) a nucleic acid sequence encoding a polypeptide comprising an amino acid sequence having at least 65% identity to positions 1 to 659 of SEQ ID NO:2;

(b) a nucleic acid sequence comprising at least 65% homology with nucleotides 137 to 2116 of SEQ ID NO:1;

(c) a nucleic acid sequence which hybridizes under low stringency conditions with (i) the nucleic acid sequence of SEQ ID NO:1, (ii) the cDNA sequence of SEQ ID NO: 1, (iii) a subsequence of (i) or (ii) of at least 100 nucleotides, or (iv) a complementary strand of (i), (ii), or (iii);

(d) an allelic variant of (a), (b), or (c);

(e) a subsequence of (a), (b), (c), or (d), wherein the subsequence encodes a polypeptide fragment which exhibits amylopullulanase activity; and (f) a polypeptide having an enzymatic activity optimum at 95° C.–105° C. at pH 5.5.

The present invention also relates to nucleic acid constructs, vectors, and host cells comprising the nucleic acid sequences as well as recombinant methods for producing the polypeptides.

BRIEF DESCRIPTION OF DRAWINGS

The present invention is further illustrated by reference to the accompanying drawings

DETAILED DISCLOSURE OF THE INVENTION

The Microorganism

Figure 1:
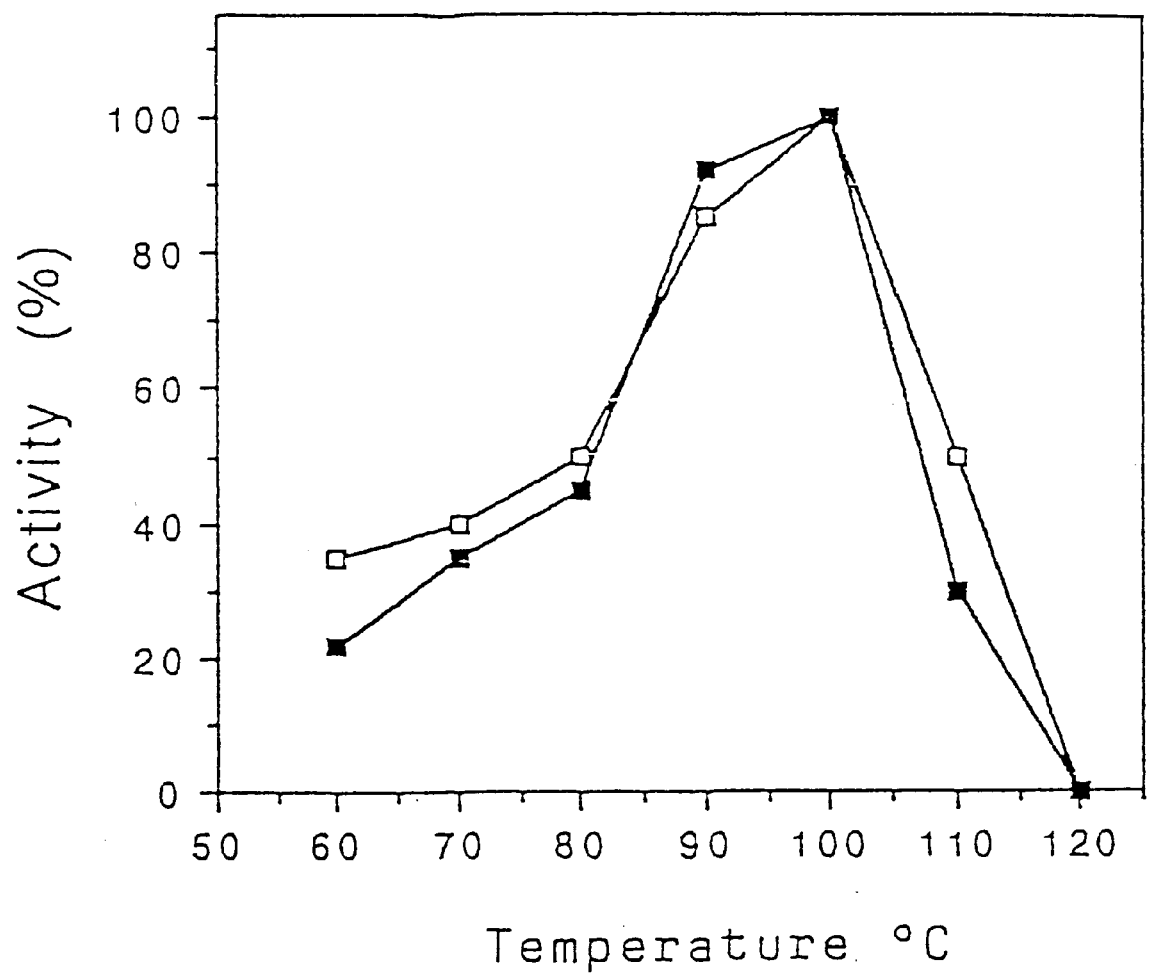
FIG. 1 shows the relative activity (% rel.) of an amylase (□) and a pullulanase (■) of the invention at various temperatures (determined at pH 5.5 with starch and pullulan, respectively, as substrate).

According to the invention, amylase is derived from an amylase producing strain of *Desulfurococcus mucosus* and pullulanase is derived from a pullulanase producing strain of *Desulfurococcus mucosus*.

A strain representative of *Desulfurococcus mucosus* has been made publicly available under Accession No. DSM 2162. The number is published in the DSM Catalogue of Strains, 1993.

Production of the Enzyme of the Invention

The enzymes of the invention may be produced by anaerobic cultivation of the above mentioned strain on a nutrient medium containing suitable carbon and nitrogen sources, such media being known in the art. Anaerobic conditions may be achieved during the preparation of media by sparging with $N_2$ and following the anaerobic techniques as described by Balch and Wolfe in *Appl. Env. Microbiol.* 32, 1976, pp. 781–791.

Alternatively, the enzymes of the invention can be produced by aerobic cultivation of a transformed host organism containing the appropriate genetic information from the above mentioned strain. Such transformants can be prepared and cultivated by methods known in the art.

The enzymes of the invention may be recovered by removing the cells from the fermentation medium (e.g., by centrifugation or filtration) and then concentrating the broth (e.g., by ultrafiltration). If desired, the enzyme may be farther purified by known methods.

The Isolated Enzymes

The enzyme of the invention can be characterized by having amylase and pullulanase activity at temperatures of from below 60° C. to approximately 120° C., having activity optimum at temperatures in the range 95–105° C., determined at pH 5.5 with the appropriate substrate. The amylopullulanase can also be characterized by having amylase and pullulanase activity at pH values of from below pH 4.0 to approximately pH 11.0, having optimum in the range pH 5.5 to pH 6.5, determined at 90° C. with starch or pullulan, respectively, as substrate.

Isolated Nucleic Acid Sequences Encoding Polypeptides Having Amylopullulanase Activity In an aspect the present invention relates to isolated nucleic acid sequences encoding polypeptides having amylopullulanase activity, selected from the group of:

(a) a nucleic acid sequence encoding a polypeptide comprising at least 65% identity to positions 1 to 659 of SEQ ID NO:2;

(b) a nucleic acid sequence comprising at least 65% homology with nucleotides 137 to 2116 of SEQ ID NO:1;

(c) a nucleic acid sequence which hybridizes under low stringency conditions with (i) the nucleic acid sequence of SEQ ID NO: 1, (ii) the cDNA sequence of SEQ ID NO: 1, (iii) a subsequence of (i) or (ii) of at least 100 nucleotides, or (iv) a complementary strand of (i), (ii), or (iii);

(d) an allelic variant of (a), (b), or (c);

(e) a subsequence of (a), (b), (c), or (d), wherein the subsequence encodes a polypeptide fragment which has amylopullulanase activity; and (f) a polypeptide having an enzymatic activity optimum at 95° C–105° C. at pH 5.5.

The term "amylopullulanase activity" is defined herein as a combined amylase and pullulanase activity. For purposes of the present invention, amylopullulanase activity is determined according to the procedure described above.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

In an embodiment, the present invention relates to isolated nucleic acid sequences encoding polypeptides having an amino acid sequence which has a degree of identity to amino acids 1 to 659 of SEQ ID NO:2 (i.e., the mature polypeptide) of at least about 65%, preferably at least about 70%, more preferably at least about 80%, even more preferably at least about 90%, most preferably at least about 95%, and even most preferably at least about 97%, which have amylopullulanase activity (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from amino acids 1 to 659 of SEQ ID NO:2.

For purposes of the present invention, the degree of homology (identity) between two nucleic acid sequences is determined by the Clustal method (Thompson, J. D., Higgins, D. G., and Gibson, T. J., (1994), Nucleic Acids research 22, 4673–4680) with an PAM250 residue table, and the default settings of the Megalign program in the Lasergene package (DNAstart Inc., 1228 South Park Street, Madison, Wis. 53715). The settings for multiple alignment are; gap penalty of 10, and a gap length penalty of 10 while the pairwise alignment parameters are gap penalty of 3 and Ktuple of 1.

Preferably, the nucleic acid sequences of the present invention encode polypeptides that comprise the amino acid sequence of SEQ ID NO: 2 or an allelic variant thereof; or a fragment thereof that has amylopullulanase activity. In a more preferred embodiment, the nucleic acid sequence of the present invention encodes a polypeptide that comprises the amino acid sequence of SEQ ID NO: 2. In another preferred embodiment, the nucleic acid sequence of the present invention encodes a polypeptide that comprises amino acids 1 to 659 of SEQ ID NO:2, which is the mature polypeptide of SEQ ID NO: 2, or an allelic variant thereof; or a fragment thereof that has amylopullulanase activity. In another preferred embodiment, the nucleic acid sequence of the present invention encodes a polypeptide that comprises amino acids 1 to 659 of SEQ ID NO: 2. In another preferred embodiment, the nucleic acid sequence of the present invention encodes a polypeptide that consists of the amino acid sequence of SEQ ID NO: 2 or an allelic variant thereof; or a fragment thereof, wherein the polypeptide fragment has amylopullulanase activity. In another preferred embodiment, the nucleic acid sequence of the present invention encodes a polypeptide that consists of the amino acid sequence of SEQ ID NO: 2.

The present invention also encompasses nucleic acid sequences which encode a polypeptide having the amino acid sequence of SEQ ID NO:2, which differ from SEQ ID NO: 1 by virtue of the degeneracy of the genetic code. The present invention also relates to subsequences of SEQ ID NO: 1 which encode fragments of SEQ ID NO:2 which have amylopullulanase activity.

A subsequence of SEQ ID NO: 1 is a nucleic acid sequence encompassed by SEQ ID NO: 1 except that one or more nucleotides from the 5' and/or 3' end have been deleted. Preferably, a subsequence contains at least 300 nucleotides, more preferably at least 60 nucleotides, and most preferably at least 18 nucleotides. A fragment of SEQ ID NO:2 is a polypeptide having one or more amino acids deleted from the amino and/or carboxy terminus of this amino acid sequence. Preferably, a fragment contains at least 100 amino acid residues, more preferably at least 20 amino acid residues, and most preferably at least 6 amino acid residues.

An allelic variant denotes any of two or more alternative forms of a gene occupying the same chomosomal locus. Allelic variation arises naturally through mutation, and may result in polymorphism within populations. Gene mutations can be silent (no change in the encoded polypeptide) or may encode polypeptides having altered amino acid sequences. The allelic variant of a polypeptide is a polypeptide encoded by an allelic variant of a gene.

The amino acid sequences of the homologous polypeptides may differ from the amino acid sequence of SEQ ID NO:2 or the mature polypeptide thereof by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (such as arginine, lysine and histidine), acidic amino acids (such as glutamic acid and aspartic acid), polar amino acids (such as glutamine and asparagine), hydrophobic amino acids (such as leucine, isoleucine and valine), aromatic amino acids (such as phenylalanine, tryptophan and tyrosine), and small amino acids (such as glycine, alanine, serine, threonine and methionine). Amino acid substitutions which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In a second embodiment, the present invention relates to isolated nucleic acid sequences which have a degree of homology to the mature polypeptide coding sequence of SEQ ID NO: 1 (i.e., nucleotides 137 to 2116) of at least about 65%, preferably about 70%, preferably about 80%, more preferably about 90%, even more preferably about 95%, and most preferably about 97% homology, which encode an active polypeptide; or allelic variants and subsequences of SEQ ID NO: 1 which encode polypeptide fragments which have amylopullulanase activity.

For purposes of the present invention, the degree of homology (identity) between two protein acid sequences is determined by the Clustal method (Thompson, J. D., Higgins, D. G., and Gibson, T. J., (1994), Nucleic Acids research 22, 4673–4680) with an PAM250 residue table, and the default settings of the Megalign program in the Lasergene package (DNAstart Inc., 1228 South Park Street, Madison, Wis. 53715). The settings for multiple alignment are; gap penalty of 10, and a gap length penalty of 10 while the pairwise alignment parameters are gap penalty of 3 and Ktuple of 1.

In a third embodiment, the present invention relates to isolated nucleic acid sequences encoding polypeptides having amylopullulanase activity which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with (i) the nucleic acid sequence of SEQ ID NO: 1, (ii) the cDNA sequence of SEQ ID NO: 1, (iii) a subsequence of (i) or (ii), or (iv) a complementary strand of (i), (ii), or (iii) (J. Sambrook, E. F. Fritsch, and T. Maniatus, 1989, Molecular Cloning, A Laboratory Manual, 2d edition, Cold Spring Harbor, N.Y.). The subsequence of SEQ ID NO: 1 may be at least 100 nucleotides or preferably at least 200 nucleotides. Moreover, the subsequence may encode a polypeptide fragment which has amylopullulanase activity.

The nucleic acid sequence of SEQ ID NO: 1 or a subsequence thereof, as well as the amino acid sequence of SEQ ID NO:2 or a fragment thereof, may be used to design a nucleic acid probe to identify and clone DNA encoding polypeptides having amylopullulanase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labelled for detecting the corresponding gene (for example, with 32P, 3H, 35S, biotin, or avidin). Such probes are encompassed by the present invention.

Thus, a genomic DNA or cDNA library prepared from such other organisms may be screened for DNA which hybridizes with the probes described above and which encodes a polypeptide having amylopullulanase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 1 or a subsequence thereof, the carrier material is used in a Southern blot. For purposes of the present invention, hybridization indicates that the nucleic acid sequence hybridizes to a nucleic acid probe corresponding to the nucleic acid sequence shown in SEQ ID NO: 1, its complementary strand, or a subsequence thereof, under very low to very high stringency conditions. Molecules to which the nucleic acid probe hybridizes under these conditions are detected using X-ray film.

In a preferred embodiment, the nucleic acid probe is nucleotides 137 to 2116 of SEQ ID NO: 1. In another preferred embodiment, the nucleic acid probe is a nucleic acid sequence which encodes the polypeptide of SEQ ID NO:2, or a subsequence thereof. In another preferred embodiment, the nucleic acid probe is SEQ ID NO: 1. In another preferred embodiment, the nucleic acid probe is the nucleic acid sequence contained in plasmid pBK-CMV which is contained in *Escherichia coli* NN049463 (DSMZ 12741, deposited on 17.03.99), wherein the nucleic acid sequence encodes a polypeptide having amylopullulanase activity. In another preferred embodiment, the nucleic acid probe is the mature polypeptide coding region of SEQ ID NO: 1 contained in plasmid pBK-CMV which is contained in *Escherichia coli* NN049463 (DSM no. 12741, deposited on 17.03.99).

For long probes of at least 100 nucleotides in length, very low to very high stringency conditions are defined as prehybridization and hybridization at 42° C. in 5×SSPE, 0.3% SDS, 200 mg/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing posthybridization at 5° C. to 10° C. below the calculated Tm using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated Tm.

The present invention also relates to isolated nucleic acid sequences produced by (a) hybridizing a DNA under very low, low, medium, medium-high, high, or very high stringency conditions with the sequence of SEQ ID NO: 1, or its complementary strand, or a subsequence thereof; and (b) isolating the nucleic acid sequence. The subsequence is preferably a sequence of at least 100 nucleotides such as a sequence which encodes a polypeptide fragment which has amylopullulanase activity.

In a fourth embodiment, the present invention relates to isolated nucleic acid sequences encoding polypeptides with amylopullulanase activity having the following physicochemical properties: Enzymatic activity optimum at 95° C.–105° C. at pH 5.5. "Enzymatic activity" optimum is determined using the amylase and/or pullulanase assay described above.

The polypeptides encoded by the isolated nucleic acid sequences of the present invention have at least 20%, preferably at least 40%, more preferably at least 60%, even more preferably at least 80%, even more preferably at least 90%, and most preferably at least 100% of the amylopullulanase activity of the mature polypeptide of SEQ ID NO:2.

The nucleic acid sequences of the present invention may be obtained from microorganisms of any genus. For purposes of the present invention, the term "obtained from" as used herein in connection with a given source shall mean that the polypeptide encoded by the nucleic acid sequence is produced by the source or by a cell in which the nucleic acid sequence from the source has been inserted.

The nucleic acid sequences of the present invention are obtained from a Desulfurococcus strain, preferably a *Desulfurococcus mucosus* strain, especially a deposited *Desulfurococcus mucosus* DSM 2162 strain or the deposited *Escherichia coli* NN049463 (DSM no. 12741, deposited on 17.03.99).

In a more preferred embodiment, the nucleic acid sequences are obtained from Desulfurococcus strain, preferably a *Desulfurococcus mucosus* strain, especially a deposited *Desulfurococcus mucosus* DSM 2162 strain, e.g., the nucleic acid sequence set forth in SEQ ID NO: 1. In another more preferred embodiment, the nucleic acid sequence is the sequence contained in plasmid pBK-CMV which is contained in *Escherichia coli* NN049463 (DSM no. 12741, deposited on 17.03.99). In another preferred embodiment, the nucleic acid sequence is nucleotides 137 to 2116 of SEQ ID NO: 1, which encodes a mature polypeptide.

Furthermore, such nucleic acid sequences may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

The present invention also relates to mutant nucleic acid sequences comprising at least one mutation in the mature polypeptide coding sequence of SEQ ID NO: 1, in which the mutant nucleic acid sequence encodes a polypeptide which consists of amino acids 1 to 659 of SEQ ID NO:2.

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, PCR: A Guide to Methods and Application, Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of [Genus], or another or related organism and thus, for example, may be an allelic or species variant of the polypeptide encoding region of the nucleic acid sequence.

Modification of a nucleic acid sequence of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant sequence may be constructed on the basis of the nucleic acid sequence presented as the polypeptide encoding part of SEQ ID NO: 1, e.g., a subsequence thereof, and/or by introduction of nucleotide substitutions which do not give rise to another amino acid sequence of the polypeptide encoded by the nucleic acid sequence, but which corresponds to the codon usage of the host organism intended for production of the enzyme, or by introduction of nucleotide substitutions which may give rise to a different amino acid sequence. For a general description of nucleotide substitution, see, e.g., Ford et al., 1991, Protein Expression and Purification 2:95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, Science 244:1081–1085). In the latter technique, mutations are introduced at every positively charged residue in the molecule, and the resultant mutant molecules are tested for amylopullulanase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, Science 255:306–312; Smith et al., 1992, Journal of Molecular Biology 224:899–904; Wlodaver et al., 1992, FEBS Letters 309:59–64).

A nucleic acid sequence of the present invention may also encode fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Methods for Producing Mutant Nucleic Acid Sequences

The present invention further relates to methods for producing a mutant nucleic acid sequence, comprising introducing at least one mutation into the mature polypeptide coding sequence of SEQ ID NO: 1 or a subsequence thereof, wherein the mutant nucleic acid sequence encodes a polypeptide which consists of amino acids 1 to 659 of SEQ ID NO:2 or a fragment thereof which has amylopullulanase activity.

The introduction of a mutation into the nucleic acid sequence to exchange one nucleotide for another nucleotide may be accomplished by site-directed mutagenesis using any of the methods known in the art. Particularly useful is the procedure which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used.

Nucleic Acid Constructs

The present invention also relates to nucleic acid constructs comprising a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The term "control sequences" is defined herein to include all components which are necessary or advantageous for the expression of a polypeptide of the present invention. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the expression of a polypeptide.

The control sequence may be an appropriate promoter sequence, a nucleic acid sequence which is recognized by a host cell for expression of the nucleic acid sequence. The promoter sequence contains transcriptional control sequences which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xy1A and xy1B genes, and prokaryotic beta-lactamase gene (Villa-Kamaroff et al., 1978, Proceedings of the National Academy of Sciences USA 75:3727–3731), as well as the tac promoter (DeBoer et al., 1983, Proceedings of the National Academy of Sciences USA 80:21–25). Further promoters are described in "Useful proteins from recombinant bacteria" in Scientific American, 1980, 242:74–94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, Yeast 8:423–488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, Molecular Cellular Biology 15:5983–5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for Bacillus NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, Microbiological Reviews 57:109–137.

Effective signal peptide coding regions for filamentous fungal host cells are the signal peptide coding regions obtained from the genes for Aspergillus oryzaeTAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

In a preferred embodiment, the signal peptide coding region is nucleotides 56 to 136 of SEQ ID NO:1 which encodes amino acids −1 to −27 of SEQ ID NO:2.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for Bacillus subtilis alkaline protease (aprE), Bacillus subtilis neutral protease (nprT), Saccharomyces cerevisiae alpha-factor, Rhizomucor miehei aspartic proteinase, and Myceliophthora thermophila laccase (WO 95/33836).

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, Aspergillus niger glucoamylase promoter, and the Aspergillus oryzae glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from Bacillus subtilis or Bacillus licheniformis, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. Preferred for use in an Aspergillus cell are the amdS and pyrG genes of Aspergillus nidulans or Aspergillus oryzae and the bar gene of Streptomyces hygroscopicus.

The vectors of the present invention preferably contain an element(s) that permits stable integration of the vector into the host cell genome or autonomous replication of the vector in the cell independent of the genome of the cell.

For integration into the host cell genome, the vector may rely on the nucleic acid sequence encoding the polypeptide or any other element of the vector for stable integration of the vector into the genome by homologous or non-homologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in E. coli, and pUB110, pE194, pTA1060, and pAMβ1 permitting replication in Bacillus. Examples of origins of replication for use in a yeast host cell are the 2 micron origin of replication, ARS1, ARS4, the combination of ARS 1 and CEN3, and the combination of ARS4 and CEN6. The origin of replication may be one having a mutation which makes its functioning temperature-sensitive in the host cell (see, e.g., Ehrlich, 1978, Proceedings of the National Academy of Sciences USA 75:1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular cells are bacterial cells such as gram positive bacteria including, but not limited to, a Bacillus cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a Streptomyces cell, e.g., *Streptomyces lividans* or *Streptomyces murinus*, or gram negative bacteria such as *E. coli* and Pseudomonas sp. In a preferred embodiment, the bacterial host cell is a *Bacillus lentus, Bacillus licheniformis, Bacillus stearothermophilus* or *Bacillus subtilis* cell. In another preferred embodiment, the Bacillus cell is an alkalophilic Bacillus.

The introduction of a vector into a bacterial host cell may, for instance, be effected by protoplast transformation (see, e.g., Chang and Cohen, 1979, Molecular General Genetics 168:111–115), using competent cells (see, e.g., Young and Spizizin, 1961, Journal of Bacteriology 81:823–829, or Dubnau and Davidoff-Abelson, 1971, Journal of Molecular Biology 56:209–221), electroporation (see, e.g., Shigekawa and Dower, 1988, Biotechniques 6:742–751), or conjugation (see, e.g., Koehler and Thorne, 1987, Journal of Bacteriology 169:5771–5278).

The host cell may be a eukaryote, such as a mammalian, insect, plant, or fungal cell.

In a preferred embodiment, the host cell is a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980).

In an even more preferred embodiment, the yeast host cell is a Candida, Hansenula, Kluyveromyces, Pichia, Saccharomyces, Schizosaccharomyces, or Yarrowia cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Knuyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as Saccharomyces cerevisiae is by budding of a unicellular thallus and carbon catabolism may be fermentative.

In an even more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladium, or Trichoderma.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens* or *Humicola lanuginosa* cell. In another most preferred embodiment, the filamentous fungal host cell is a *Mucor miehei* cell. In another most preferred embodiment, the filamentous fungal host cell is a *Myceliophthora thermophila* cell. In another most preferred embodiment, the filamentous fungal host cell is a *Neurospora crassa* cell. In another most preferred embodiment, the filamentous fungal host cell is a *Penicillium purpurogenum* cell. In another most preferred embodiment, the filamentous fungal host cell is a *Thielavia terrestris* cell. In another most preferred embodiment, the Trichoderma cell is a *Trichoderma harzianum, Trichoderma koningii, Trichoderma longibrachiatum, Trichoderma reesei* or *Trichoderma viride* cell.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, Proceedings of the National Academy of Sciences USA 81:1470–1474. Suitable methods for transforming Fusarium species are described by Malardier et al., 1989, Gene 78:147–156 and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182–187, Academic Press, Inc., New York; Ito et al., 1983, Journal of Bacteriology 153:163; and Hinnen et al., 1978, Proceedings of the National Academy of Sciences USA 75:1920.

Methods of Production

The present invention also relates to methods for producing a polypeptide comprising (a) cultivating a host cell under conditions suitable for production of the polypeptide; and (b) recovering the polypeptide.

The present invention also relates to methods for producing a polypeptide of the present invention comprising (a) cultivating a host cell under conditions conducive for production of the polypeptide, wherein the host cell comprises a mutant nucleic acid sequence having at least one mutation in the mature polypeptide coding region of SEQ ID NO: 1, wherein the mutant nucleic acid sequence encodes a polypeptide which consists of amino acids 1 to 659 of SEQ ID NO:2, and (b) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, enzyme assays may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J. -C. Janson and Lars Ryden, editors, VCH Publishers, New York, 1989).

Uses

The present invention is also directed to methods of using the polypeptides having amylopullulanase activity. The enzymes of this invention possess valuable properties allowing for various industrial applications. In particular the enzymes, in being thermostable, find potential application in the production of sweeteners and ethanol from starch. Conditions for conventional starch converting processes and liquefaction and/or saccharification processes are described in for instance U.S. Pat. No. 3,912,590 and EP patent publications Nos. 252,730 and 63,909.

Further method of use contemplated include using homologous enzymes or recombinant enzymes of the invention for starch conversion processes, especially in the liquefaction step; in baking; for production of branched oligosaccharides; for oil drilling; and for production of maltodextrins.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

Materials and Methods

Deposit of Biological Material

The following biological material has been deposited under the terms of the Budapest Treaty with the Deutsche Sammlung Von Mikroorganismen, und Zellkulturen GmbH (DSMZ), Mascheroder Weg 1b, D-38124 Braunschweig, GERMANY, and given the following accession number:

| Deposit | *Escherichia coli* NN049463 |
|---|---|
| Accession Number | DSM no. 12741 |
| Date of Deposit | 17.03.99 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

Determination of Amylase Activity

Amylase activity is determined by measuring the amount of reducing sugar released during the incubation with starch. One unit (U) of amylase activity is defined as the amount of amylase that releases 1 $\mu$mole of reducing sugar (as maltose standard) per min. under the following assay conditions: A 0.05 ml volume of 1% soluble starch is added to 0.05 ml of 0.1 M sodium acetate buffer pH 5.5. 25 $\mu$l of enzyme solution are added to this mixture and the sample is incubated at 90° C. for 30 min. The reaction is stopped by cooling on ice, and the amount of reducing sugar is determined by dinitrosalicylic acid (DNS). Sample blanks are used to correct for nonenzymatic release of reducing sugar.

Determination of Pullulanase Activity I

Pullulanase activity is determined by measuring the amount of reducing sugar released during the incubation with pullulan. One unit (U) of pullulanase activity is defined as the amount of pullulanase that releases 1 [mole of reducing sugar (as maltose standard) per min. under the following assay conditions: A 0.05 ml volume of 1% pullulan is added to 0.05 ml of 0.1 M sodium acetate buffer pH 5.5. 25 µl of enzyme solution are added to this mixture and the sample is incubated at 90° C. for 30 min. The reaction is stopped by cooling on ice, and the amount of reducing sugar is determined by dinitrosalicylic acid. Sample blanks are used to correct for nonenzymatic release of reducing sugar.

The following example further illustrates the present invention, and it is not intended to be in any way limiting to the scope of the invention as claimed.

EXAMPLE 1

Cultivation of Desulfurococcus, DSM 2162

The strain *Desulfurococcus mucosus*, DSM 2162, was recultured from glycerol-preserved cells using the medium recommended by the Deutsche Sammlung von Mikroorganismen (DSM). The microorganisms were grown in 1 liter batch cultures under the following conditions: Medium: DSM184 (DSM184 is described in DSM Catalogue of Strains, 1993), pH 5.8, temp. 85° C.; in the medium sulphur and tryptone were omitted and starch (0.5% w/v) was added as the only carbohydrate; yeast extract concentration was 0.1% (w/v). The cell density achieved in this medium was $\geq 10^8$ cells/ml. Anaerobic conditions were achieved during the preparation of media by sparging with $N_2$ and following the techniques as described by Balch in Appl. Env. Microbiol. 32, 1976, pp. 781–791.

After cultivation the culture fluid was centrifuged at 12.000×g for 30 minutes at 4° C., and the cell free supernatant was concentrated up to 100-fold using an Amicon Ultrafiltration System. The cell pellet was resuspended in 50 mM sodium acetate buffer pH 5.5 and sonicated three times for 3 minutes at 50% duty cycle by a BRANSON 450 sonifier. The cell debris was separated from the supernatant after centrifugation at 10.000×g for 30 minutes at 4° C.

The following total activity (U) in both supernatant and cell extract was found:

Amylase activity: 2.0 U/l
Pullulanase activity: 0.8 U/l
Temperature Optima

Temperature optima were determined by incubation of samples for 30 minutes at pH 5.5 at temperatures from 60° C. to 120° C. The incubation was conducted in closed Hungate tubes in order to prevent boiling of the solution.

FIG. 1 shows the result (Amylase (□) and pullulanase (■)).

pH Optima

To determine pH optima, Universal buffer (Britten and Robinson) was used to obtain values from pH 4.0 to pH 11.0. Samples were incubated for 30 minutes at 90° C. at the pH in question.

Figure 2:
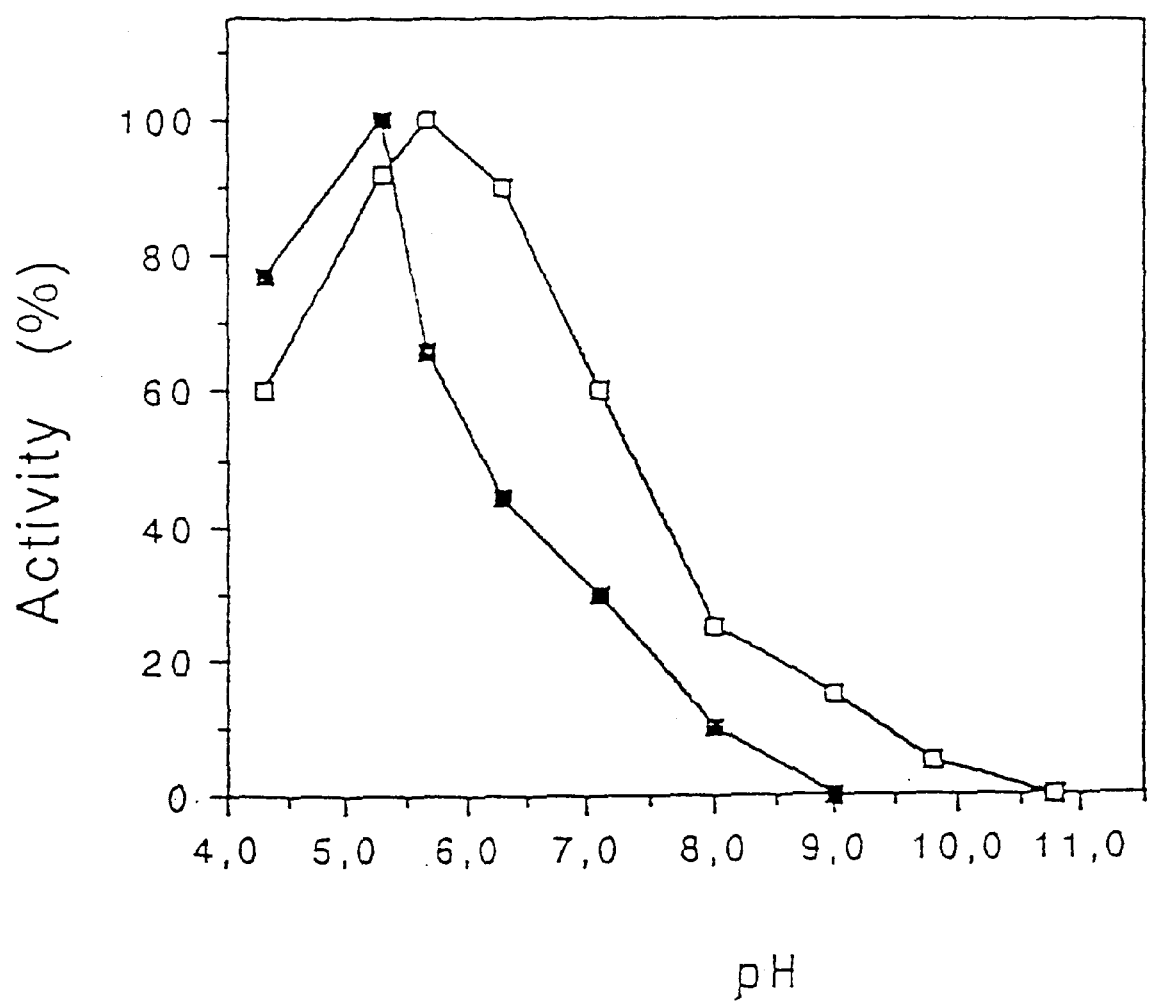
FIG. 2 shows the relative activity (% rel.) of an amylase (□) and a pullulanase (■) of the invention at various pH, determined at 90° C. with starch and pullulan, respectively, as substrate.

FIG. 2 shows the result (Amylase (") and pullulanase (§)).

EXAMPLE 3

DNA isolation from archaea grown in sulfur

DNA was isolated from *Desulfurococcus mucosus* cells supplied by the Technical University Hamburg-Harburg. The method used was Protocol 14, Ramakrishnan and Adams, p. 95 in "Archaea, A laboratory manual, Thermophiles" eds. F. T. Robb, A. R. Place, Cold Spring Harbour Laboratory Press, 1995

1. Cells were spun for 15 minutes at 4,200 rpm.
2. 3 ml cell suspension buffer was added to both samples and then 15 ml RNase A+T (10 mg/ml) and 300 µl 15% SDS.
3. The solution was incubated at 55° C. for 15 minutes and then 75 µl protease mixture was added and incubated further for 1 hour.
4. 1.5 ml "Salt Out" BIO101 was added to each tube and left on ice for 10 minutes.
5. The DNA containing solution was divided into microfuge tubes and centrifuged for 20 minutes at 20,000 rpm, 4° C.
6. The supernatant was transferred to a larger tube and 6 ml TE pH 8.0 and 24 ml cold ethanol was added.
7. The DNA was fished out with a glass hook, washed twice in 70% ethanol and dried.
8. The DNA was resuspended in 5 ml of TE pH 8.0.

The DNA was partially digested with Sau3A and fractionated on an agarose gel. Fractions between 1.5–8 kb were used for making the DNA library in ZAP express (Stratagene). Phagemids were excised as described in the instructions for users.

Screening of the *D. mucosus* library, SBL0531 and sequencing of the positive clone The library (7100 clones) was grown in microtitre plates inoculated at 0.7 cfu/well. The assay plates contained 150 µl AZCL-amylose (0.07% w/v)+AZCL-pullulan (0.07% w/v) (Megazyme) in 50 mM sodium acetate buffer pH 5.5 and were incubated at 80° C. for 24–48 hours. Positive clones (identified by the release of blue dye) were restreaked onto LB plates containing cibachron stained pullulan and AZCL-pullulan.

The gene was sequenced using the Primer Island Transposon Kit (purchased from Applied Biosystems) and selecting for pullulanase negative, trimethoprim+kanamycin resistant clones (due to transposon insertion).

Cloning and sequence analysis of the amylopullulanase from *Desulfurococcus mucosus* in *E. coli*

Screening of the excised λZAP gene library yielded amylopullulanase positive clones. One of these, *E. coli* AMY1011, was chosen for further work. *E. coli* AMY1011 contains the gene expressing amylopullulanase activity from *Desulfurococcus mucosus*. The DNA sequence was obtained from *E. coli* AMY1011 using the transposon sequencing method and selecting for activity loss in combination with primer walking. The insert is 3529 bp and contains one large ORF of 1974 bp (686 amino acids) with a predicted protein molecular mass of 77 kDa and 2 smaller ones of 651 bp and 360 bp. The large ORF encodes the amylopullulanase.

Figure 3:
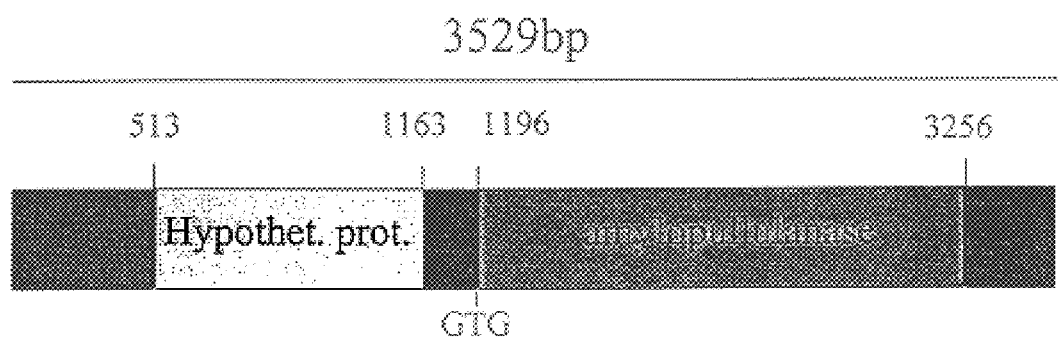
FIG. 3 shows the ORFs identified and position on the cloned insert in *E. coli* AMY1011.

The translational start site is predicted to be the GTG at position 1196 in the insert sequence (see FIG. 3). This is preceded by the putative Shine-Dalgarno sequence of GGAGGTG (nucleotides 51–57 in SEQ ID NO:1) 9–15 bp upstream from the GTG. In addition, the "TATA" motif (box A) of archaeal promoters located normally around a position of −30 and −25 relative to the transcription start could be the sequence TTTAAT (nucleotides 7–12 in SEQ ID NO: 1) present 29 bp upstream from the Shine-Dalgarno sequence. A signal sequence of 27 amino acids cleaving between the alanine and serine was predicted.

Degradation pattern on various substrates (as seen by TLC)

Figure 4:
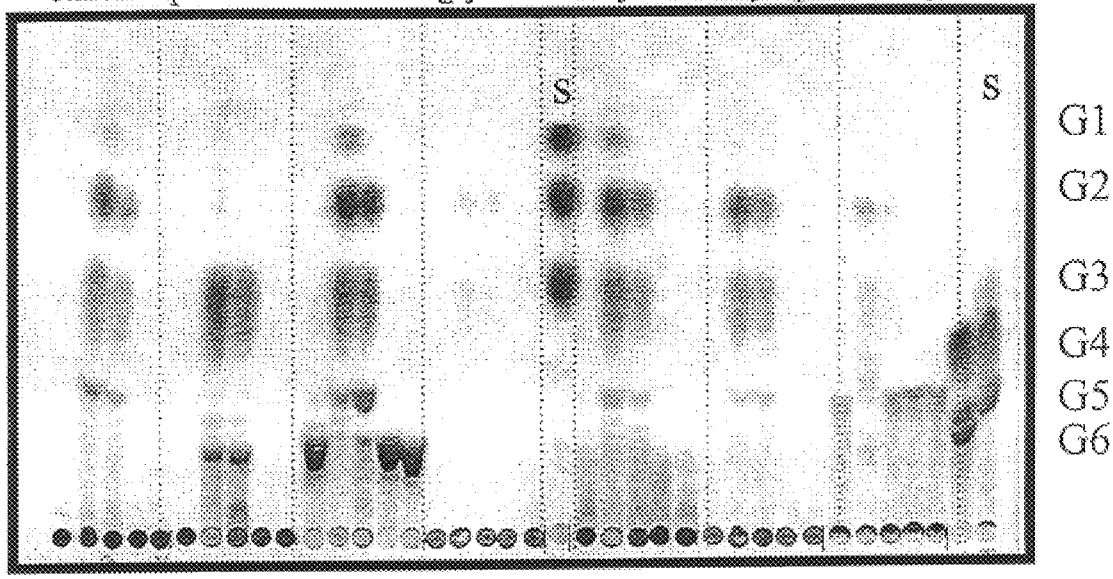
FIG. 4 shows the TLC patterns of the *D. mucosus* amylopullulanase produced in *E. coli* AMY1011 using starch, pullulan, maltohexose, glycogen, amylose, amylopectin and α-cyclodextrin as substrates. Lane 1, supernatant from *E. coli* AMY1011 culture; Lane 2, *E. coli* AMY1011 sonicate; Lane 3, *E. coli* AMY1011 sonicate heated at 80° C., 10 minutes; Lane 4, buffer negative control; Lane 5, medium negative control; S, standard (glucose, maltose, maltotriose) (maltotetraose, maltopentose, maltohexose).

The amylopullulanase from *D. mucosus* degrades pullulan, starch, maltohexaose, glycogen, soluble amylose, α-cyclodextrin and β-cyclodextrin to G1, G2, G3 and oligosaccharides (See FIG. 4).

Heat stability

The enzyme can be heated at 80° C. for 30 minutes with no significant loss in ;activity as determined by reducing sugars measurement (DNS assay) and TLC pattern. Activity levels for 5, 10 and 15 minutes on starch (pH 6.0) at 80° C., 90° C. and 100° C. are identical as determined by reducing sugars.

Figure 5:
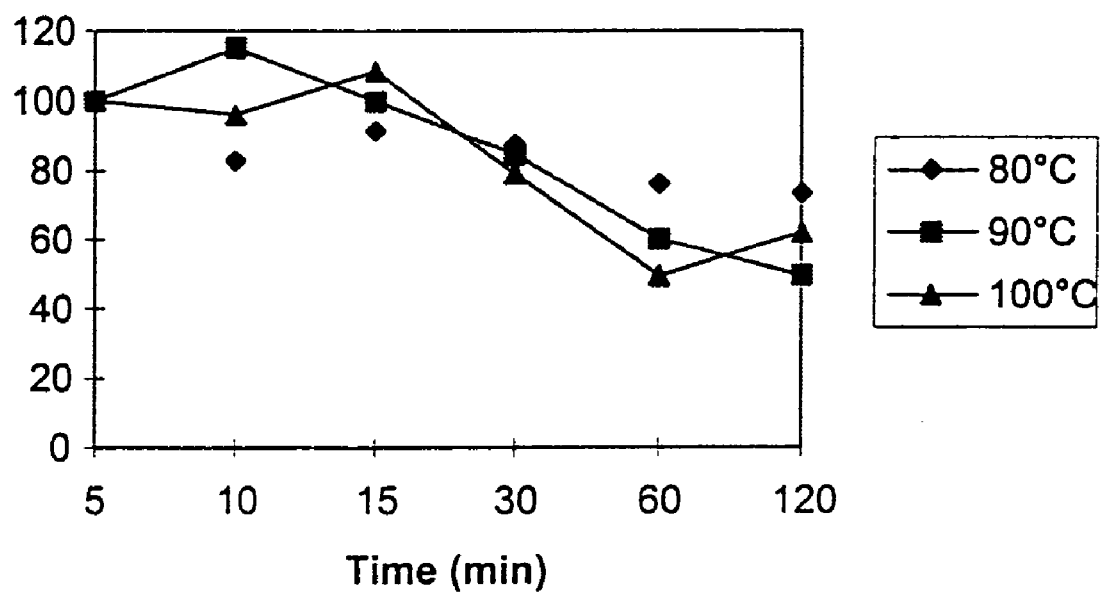
FIG. 5 shows the relative activity levels of the amylopullulanase of the invention after 5, 15, 30, 60 and 120 minutes, respectively, on starch (pH 5.5) at 80° C., 90° C. and 100° C., respectively. In addition, the enzyme demonstrated activity after autoclaving at 120° C. for 20 minutes.

The crude extract of the *E. coli* clone containing the amylopullulanase was heated at varying temperatures for varying lengths of time. Samples were stored at 4° C. and remaining activity was measured on starch at 80° C. for 30 minutes, pH 6.0 The results are shown as relative activities in FIG. 5.

We claim:

1. An isolated nucleic acid sequence encoding a polypeptide having amylopullulanase activity, selected from the group consisting of:
   (a) a nucleic acid sequence encoding a polypeptide comprising at least 65% identity with positions 1 to 659 of SEQ ID NO:2;
   (b) a nucleic acid sequence comprising at least 65% homology with nucleotides 137 to 2116 of SEQ ID NO:1;
   (c) a nucleic acid sequence which hybridizes under low stringency conditions with (i) the nucleic acid sequence of SEQ ID NO:1 or (ii) a subsequence of (i) of at least 100 nucleotides;
   (d) an allelic variant of (a), (b), or (c); and
   (e) a subsequence of (a), (b), (c) or (d), wherein the subsequence encodes a polypeptide fragment which has amylopullulanase activity; or
   a complementary strand of (i) or (ii).

2. The nucleic acid sequence of claim 1 contained in *Escherichia coli* NN049463 (DSM 12741).

3. A nucleic acid construct comprising the nucleic acid sequence of claim 1 operably linked to one or more control sequences which direct the production of the polypeptide in a suitable expression host.

4. A recombinant expression vector comprising the nucleic acid construct of claim 3, a promoter, and transcriptional and translational stop signals.

5. A recombinant host cell comprising the nucleic acid construct of claim 3.

6. A method for producing a polypeptide having amylopullulanase activity comprising (a) cultivating the host cell of claim 5 under conditions suitable for production of the polypeptide; and (b) recovering the polypeptide.

* * * * *

SEQUENCE LISTING

```
<160> NUMBER OF SEQ ID NOS: 2

<210> SEQ ID NO 1
<211> LENGTH: 2389
<212> TYPE: DNA
<213> ORGANISM: Desulfurococuss mucosus
<220> FEATURE:
<221> NAME/KEY: CDS
<222> LOCATION: (56)...(2116)
<221> NAME/KEY: sig_peptide
<222> LOCATION: (56)...(136)
<221> NAME/KEY: mat_peptide
<222> LOCATION: (137)...(2116)
<221> NAME/KEY: misc_feature
<222> LOCATION: (7)...(11)
<221> NAME/KEY: misc_feature
<222> LOCATION: (41)...(45)

<400> SEQUENCE: 1
cgggtgttta ataaagcttg catacatagg gcaagggtgt ggaggtgctt aacca gtg        58
                                                              Val ggc tgg agg ccg gtt gct gta tac gct act cta ata ctc gta tta ctc        106
Gly Trp Arg Pro Val Ala Val Tyr Ala Thr Leu Ile Leu Val Leu Leu
    -25                 -20                 -15 cag ttg acg ccc cta cct atc gct ggt gcg agc atc atg gag ata tat        154
Gln Leu Thr Pro Leu Pro Ile Ala Gly Ala Ser Ile Met Glu Ile Tyr
-10                  -5                   1               5 gtc gcc gat gac cag gtc acc gtg gta cac aac ccc ctg gat cca gca        202
Val Ala Asp Asp Gln Val Thr Val Val His Asn Pro Leu Asp Pro Ala
                10                  15                  20 tac ctt tca gca gcc gac ggc tat ttg atc ccg agg ata agg gtg gcc        250
Tyr Leu Ser Ala Ala Asp Gly Tyr Leu Ile Pro Arg Ile Arg Val Ala
            25                  30                  35 agc agc ctg gat gtt gcc tct ggg acg ctg gta gct gat aaa gga gag        298
Ser Ser Leu Asp Val Ala Ser Gly Thr Leu Val Ala Asp Lys Gly Glu
        40                  45                  50 tac cag ttg aaa ccc cag ttg gcg acg aac acg tgg aga gta tac tat        346
Tyr Gln Leu Lys Pro Gln Leu Ala Thr Asn Thr Trp Arg Val Tyr Tyr
55                  60                  65                  70 gcc aca ata ccc att ggt gag gca tcc agg ggt tta aac tac tat ttc        394
Ala Thr Ile Pro Ile Gly Glu Ala Ser Arg Gly Leu Asn Tyr Tyr Phe
                75                  80                  85 aag ctc acc ctg cgg aac aac act gtg gtg tac gtg tat aat gcg acg        442
Lys Leu Thr Leu Arg Asn Asn Thr Val Val Tyr Val Tyr Asn Ala Thr
            90                  95                  100 gcg agc agg cta ttc aac ttc aat ggg tca ata gtt ttc agg cag gtg        490
Ala Ser Arg Leu Phe Asn Phe Asn Gly Ser Ile Val Phe Arg Gln Val
        105                 110                 115 gag tgg gtt aag agc cgg gtt ggc tac cag ata ttc ccc gat aga ttc        538
Glu Trp Val Lys Ser Arg Val Gly Tyr Gln Ile Phe Pro Asp Arg Phe
```

```
                 120                      125                      130
tac aat ggt gat cca agc aac gat tta aag gcc aac cta acg gat gag           586
Tyr Asn Gly Asp Pro Ser Asn Asp Leu Lys Ala Asn Leu Thr Asp Glu
135                      140                      145                  150 cta tgg ata aac gag gtt tca agg ggc gta ccc gta ttc act agg tgg           634
Leu Trp Ile Asn Glu Val Ser Arg Gly Val Pro Val Phe Thr Arg Trp
                     155                      160                      165 gat ggc cct gta aca tcg cta cat tgc tgc cac cag tat ttc ggc ggc           682
Asp Gly Pro Val Thr Ser Leu His Cys Cys His Gln Tyr Phe Gly Gly
                 170                      175                      180 gac ctg aag ggg gtc aca gag aag ctc gac tac ctc aag gag ctc ggt           730
Asp Leu Lys Gly Val Thr Glu Lys Leu Asp Tyr Leu Lys Glu Leu Gly
            185                      190                      195 gtt ggg cta ata tat ctg aac cct ata ttc ctc tcc ggc agc gta cac           778
Val Gly Leu Ile Tyr Leu Asn Pro Ile Phe Leu Ser Gly Ser Val His
        200                      205                      210 ggc tac gac act tac gac tac tat act gtg gac ccg aag ttc ggg acc           826
Gly Tyr Asp Thr Tyr Asp Tyr Tyr Thr Val Asp Pro Lys Phe Gly Thr
215                      220                      225                  230 ctg gaa gac ctt aaa acc ctc atc aac gag gcg cat aaa cgg ggc att           874
Leu Glu Asp Leu Lys Thr Leu Ile Asn Glu Ala His Lys Arg Gly Ile
                     235                      240                      245 aaa gtg ata ttc gac ttc gtc cca gac cac gtg ggg ctt gga ttc tgg           922
Lys Val Ile Phe Asp Phe Val Pro Asp His Val Gly Leu Gly Phe Trp
                 250                      255                      260 gct ttc caa gac gtt tac agg aac gga agg aac agc acg tac tgg agc           970
Ala Phe Gln Asp Val Tyr Arg Asn Gly Arg Asn Ser Thr Tyr Trp Ser
            265                      270                      275 tgg ttc ata gtg tat aag tgg agg ttc aag ctc ggg gac ccc acc gcg          1018
Trp Phe Ile Val Tyr Lys Trp Arg Phe Lys Leu Gly Asp Pro Thr Ala
        280                      285                      290 tat aag tgc tgg tgg ggg ata ggg agc ctc ccg cag ctg aat gtt ctg          1066
Tyr Lys Cys Trp Trp Gly Ile Gly Ser Leu Pro Gln Leu Asn Val Leu
295                      300                      305                  310 aac act gag gtt aga cag tac ctg atc aat gta gcc cta tac tgg tta          1114
Asn Thr Glu Val Arg Gln Tyr Leu Ile Asn Val Ala Leu Tyr Trp Leu
                     315                      320                      325 agc atc ggc ttc gat ggg ttg agg att gat act ccg cta gac gtc atc          1162
Ser Ile Gly Phe Asp Gly Leu Arg Ile Asp Thr Pro Leu Asp Val Ile
                 330                      335                      340 gac tcg gag agc ttc ttc agg gag cta cgt gaa gca gtc aag tcg agg          1210
Asp Ser Glu Ser Phe Phe Arg Glu Leu Arg Glu Ala Val Lys Ser Arg
            345                      350                      355 tat ccc gac gca tac att gtt gga gag ata tgg gat tac cgt ccc gaa          1258
Tyr Pro Asp Ala Tyr Ile Val Gly Glu Ile Trp Asp Tyr Arg Pro Glu
        360                      365                      370 tgg cta agg ggc aat gca ttc gac tcc ctt atg aac tac tat tta ggc          1306
Trp Leu Arg Gly Asn Ala Phe Asp Ser Leu Met Asn Tyr Tyr Leu Gly
375                      380                      385                  390 agg aac ata ctc ctc agc tat gca cgt gga gcc ctg aac ggt tac acc          1354
Arg Asn Ile Leu Leu Ser Tyr Ala Arg Gly Ala Leu Asn Gly Tyr Thr
                     395                      400                      405 gcc tca atg aag ctt gct gaa tac tat gcc ggt ata ggt gtg aac gtg          1402
Ala Ser Met Lys Leu Ala Glu Tyr Tyr Ala Gly Ile Gly Val Asn Val
                 410                      415                      420 gct gga atg ggt ttc aac att att gga tcc cat gac acc tcc agg gtt          1450
Ala Gly Met Gly Phe Asn Ile Ile Gly Ser His Asp Thr Ser Arg Val
            425                      430                      435 ctc acg gat ctc ggc ggg gga gga ttg aac agc acc ccg agc aat gag          1498
```

```
Leu Thr Asp Leu Gly Gly Gly Leu Asn Ser Thr Pro Ser Asn Glu
    440                 445                 450 tcc ata gcc cgc tta aaa ctg ctt tca acg cta cag tat act cag ccc    1546
Ser Ile Ala Arg Leu Lys Leu Leu Ser Thr Leu Gln Tyr Thr Gln Pro
455                 460                 465                 470 ggt atg cca gta gtg ttc cag ggc gat gaa aga ggg atc act ggt aga    1594
Gly Met Pro Val Val Phe Gln Gly Asp Glu Arg Gly Ile Thr Gly Arg
                475                 480                 485 cag gga aac cat gat gag cag aga tac cct att caa tgg gat agg tta    1642
Gln Gly Asn His Asp Glu Gln Arg Tyr Pro Ile Gln Trp Asp Arg Leu
                490                 495                 500 aat gta gag gtc tac gag cac tat aag agg ctg gga gaa ctc aag aac    1690
Asn Val Glu Val Tyr Glu His Tyr Lys Arg Leu Gly Glu Leu Lys Asn
                505                 510                 515 act att cca gca ttg tca acc agt ata ata cat gtg ctg ggt gga tca    1738
Thr Ile Pro Ala Leu Ser Thr Ser Ile Ile His Val Leu Gly Gly Ser
520                 525                 530 ggc ggc ttg ctt gcc tat act agg ggg tat atg gat gaa gta ctc gtc    1786
Gly Gly Leu Leu Ala Tyr Thr Arg Gly Tyr Met Asp Glu Val Leu Val
535                 540                 545                 550 atc gcc aat aat gat gca tcc aca ccg caa tca tac gag ctg ccc ccg    1834
Ile Ala Asn Asn Asp Ala Ser Thr Pro Gln Ser Tyr Glu Leu Pro Pro
                555                 560                 565 ggc aac tgg acc ctg ata tat gct agc aat aac tgg agc gag gtc tcc    1882
Gly Asn Trp Thr Leu Ile Tyr Ala Ser Asn Asn Trp Ser Glu Val Ser
                570                 575                 580 gtc gag cac aat acg gtt aca gtg ccg cct ttg aca gcc ctg ata ctt    1930
Val Glu His Asn Thr Val Thr Val Pro Pro Leu Thr Ala Leu Ile Leu
                585                 590                 595 gtc agg aac act gtg tcc gag acc act act aca tcg aca gct gtg acc    1978
Val Arg Asn Thr Val Ser Glu Thr Thr Thr Thr Ser Thr Ala Val Thr
600                 605                 610 agc ttc ccc ggc acc atg tac acg gaa acc acc gct att cca ggc cga    2026
Ser Phe Pro Gly Thr Met Tyr Thr Glu Thr Thr Ala Ile Pro Gly Arg
615                 620                 625                 630 ctg gag cag gac acc aga gtg ctg att atc gta gta gcc gtg ccg ctg    2074
Leu Glu Gln Asp Thr Arg Val Leu Ile Ile Val Val Ala Val Pro Leu
                635                 640                 645 ctc ctt gcg aca cta gta ttg ctc cgc agg cat agg gct taa            2116
Leu Leu Ala Thr Leu Val Leu Leu Arg Arg His Arg Ala
                650                 655 cgcgtagagg agaaggcttg gagtagcgtg aaaggattaa acggtttaag ccgcctagat    2176
ataaacggcg atgaagagcc gtcgaacggc cgaagaggtg atgagtcgct ctcctccgag    2236
ccctccagat tcgcaacgaa cctagaggtt tctcaaggca tgaggcaggc tacggggcac    2296
cggttcctcg tgcaccccgg gcccgctgca ctatggattc cactgggggg ggggagccct    2356
gtcttttaag gctggatgct agtgtacttg atc                                 2389

<210> SEQ ID NO 2
<211> LENGTH: 686
<212> TYPE: PRT
<213> ORGANISM: Desulfurocucuss mucosus
<220> FEATURE:
<221> NAME/KEY: SIGNAL
<222> LOCATION: (1)...(27)

<400> SEQUENCE: 2

Val Gly Trp Arg Pro Val Ala Val Tyr Ala Thr Leu Ile Leu Val Leu
        -25                 -20                 -15
```

-continued

```
Leu Gln Leu Thr Pro Leu Pro Ile Ala Gly Ala Ser Ile Met Glu Ile
    -10              -5                   1               5

Tyr Val Ala Asp Asp Gln Val Thr Val His Asn Pro Leu Asp Pro
            10                  15                  20

Ala Tyr Leu Ser Ala Ala Asp Gly Tyr Leu Ile Pro Arg Ile Arg Val
            25                  30                  35

Ala Ser Ser Leu Asp Val Ala Ser Gly Thr Leu Val Ala Asp Lys Gly
            40                  45                  50

Glu Tyr Gln Leu Lys Pro Gln Leu Ala Thr Asn Thr Trp Arg Val Tyr
    55                  60                  65

Tyr Ala Thr Ile Pro Ile Gly Glu Ala Ser Arg Gly Leu Asn Tyr Tyr
70                  75                  80                  85

Phe Lys Leu Thr Leu Arg Asn Asn Thr Val Val Tyr Val Tyr Asn Ala
            90                  95                  100

Thr Ala Ser Arg Leu Phe Asn Phe Asn Gly Ser Ile Val Phe Arg Gln
            105                 110                 115

Val Glu Trp Val Lys Ser Arg Val Gly Tyr Gln Ile Phe Pro Asp Arg
            120                 125                 130

Phe Tyr Asn Gly Asp Pro Ser Asn Asp Leu Lys Ala Asn Leu Thr Asp
    135                 140                 145

Glu Leu Trp Ile Asn Glu Val Ser Arg Gly Val Pro Val Phe Thr Arg
150                 155                 160                 165

Trp Asp Gly Pro Val Thr Ser Leu His Cys Cys His Gln Tyr Phe Gly
                170                 175                 180

Gly Asp Leu Lys Gly Val Thr Glu Lys Leu Asp Tyr Leu Lys Glu Leu
            185                 190                 195

Gly Val Gly Leu Ile Tyr Leu Asn Pro Ile Phe Leu Ser Gly Ser Val
            200                 205                 210

His Gly Tyr Asp Thr Tyr Asp Tyr Tyr Thr Val Asp Pro Lys Phe Gly
    215                 220                 225

Thr Leu Glu Asp Leu Lys Thr Leu Ile Asn Glu Ala His Lys Arg Gly
230                 235                 240                 245

Ile Lys Val Ile Phe Asp Phe Val Pro Asp His Val Gly Leu Gly Phe
            250                 255                 260

Trp Ala Phe Gln Asp Val Tyr Arg Asn Gly Arg Asn Ser Thr Tyr Trp
            265                 270                 275

Ser Trp Phe Ile Val Tyr Lys Trp Arg Phe Lys Leu Gly Asp Pro Thr
    280                 285                 290

Ala Tyr Lys Cys Trp Trp Gly Ile Gly Ser Leu Pro Gln Leu Asn Val
    295                 300                 305

Leu Asn Thr Glu Val Arg Gln Tyr Leu Ile Asn Val Ala Leu Tyr Trp
310                 315                 320                 325

Leu Ser Ile Gly Phe Asp Gly Leu Arg Ile Asp Thr Pro Leu Asp Val
                330                 335                 340

Ile Asp Ser Glu Ser Phe Phe Arg Glu Leu Arg Glu Ala Val Lys Ser
            345                 350                 355

Arg Tyr Pro Asp Ala Tyr Ile Val Gly Glu Ile Trp Asp Tyr Arg Pro
    360                 365                 370

Glu Trp Leu Arg Gly Asn Ala Phe Asp Ser Leu Met Asn Tyr Tyr Leu
    375                 380                 385

Gly Arg Asn Ile Leu Leu Ser Tyr Ala Arg Gly Ala Leu Asn Gly Tyr
390                 395                 400                 405
```

```
                                    -continued

Thr Ala Ser Met Lys Leu Ala Glu Tyr Tyr Ala Gly Ile Gly Val Asn
            410                 415                 420

Val Ala Gly Met Gly Phe Asn Ile Ile Gly Ser His Asp Thr Ser Arg
                425                 430                 435

Val Leu Thr Asp Leu Gly Gly Gly Gly Leu Asn Ser Thr Pro Ser Asn
            440                 445                 450

Glu Ser Ile Ala Arg Leu Lys Leu Leu Ser Thr Leu Gln Tyr Thr Gln
    455                 460                 465

Pro Gly Met Pro Val Val Phe Gln Gly Asp Glu Arg Gly Ile Thr Gly
470                 475                 480                 485

Arg Gln Gly Asn His Asp Glu Gln Arg Tyr Pro Ile Gln Trp Asp Arg
                490                 495                 500

Leu Asn Val Glu Val Tyr Glu His Tyr Lys Arg Leu Gly Glu Leu Lys
                505                 510                 515

Asn Thr Ile Pro Ala Leu Ser Thr Ser Ile Ile His Val Leu Gly Gly
            520                 525                 530

Ser Gly Gly Leu Leu Ala Tyr Thr Arg Gly Tyr Met Asp Glu Val Leu
    535                 540                 545

Val Ile Ala Asn Asn Asp Ala Ser Thr Pro Gln Ser Tyr Glu Leu Pro
550                 555                 560                 565

Pro Gly Asn Trp Thr Leu Ile Tyr Ala Ser Asn Asn Trp Ser Glu Val
                570                 575                 580

Ser Val Glu His Asn Thr Val Thr Val Pro Pro Leu Thr Ala Leu Ile
                585                 590                 595

Leu Val Arg Asn Thr Val Ser Glu Thr Thr Thr Thr Ser Thr Ala Val
            600                 605                 610

Thr Ser Phe Pro Gly Thr Met Tyr Thr Glu Thr Thr Ala Ile Pro Gly
    615                 620                 625

Arg Leu Glu Gln Asp Thr Arg Val Leu Ile Ile Val Val Ala Val Pro
630                 635                 640                 645

Leu Leu Leu Ala Thr Leu Val Leu Leu Arg Arg His Arg Ala
            650                 655
```